US00PP33822P2

(12) United States Plant Patent
Beekenkamp

(10) Patent No.: US PP33,822 P2
(45) Date of Patent: Jan. 4, 2022

(54) POINSETTIA PLANT NAMED 'BKPONVW'

(50) Latin Name: ***Euphorbia pulcherrima* Willd.**
Varietal Denomination: BKPONVW

(71) Applicant: Annie Cornelia Beekenkamp, Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/171,265

(22) Filed: Feb. 9, 2021

(51) Int. Cl.
*A01H 5/12* (2018.01)
*A01H 6/38* (2018.01)

(52) U.S. Cl.
USPC ..... Plt./304

(58) Field of Classification Search
USPC ..... Plt./302, 303, 304, 305
See application file for complete search history.

*Primary Examiner* — Susan McCormick Ewoldt
(74) *Attorney, Agent, or Firm* — C. Anne Whealy

(57) ABSTRACT

A new and distinct cultivar of Poinsettia plant named 'BKPONVW', characterized by its broadly upright and uniformly mounding plant habit; moderately vigorous growth habit; freely branching habit; dark green-colored leaves; large and full inflorescences with white-colored flower bracts; and excellent post-production longevity.

2 Drawing Sheets

Figure 1:
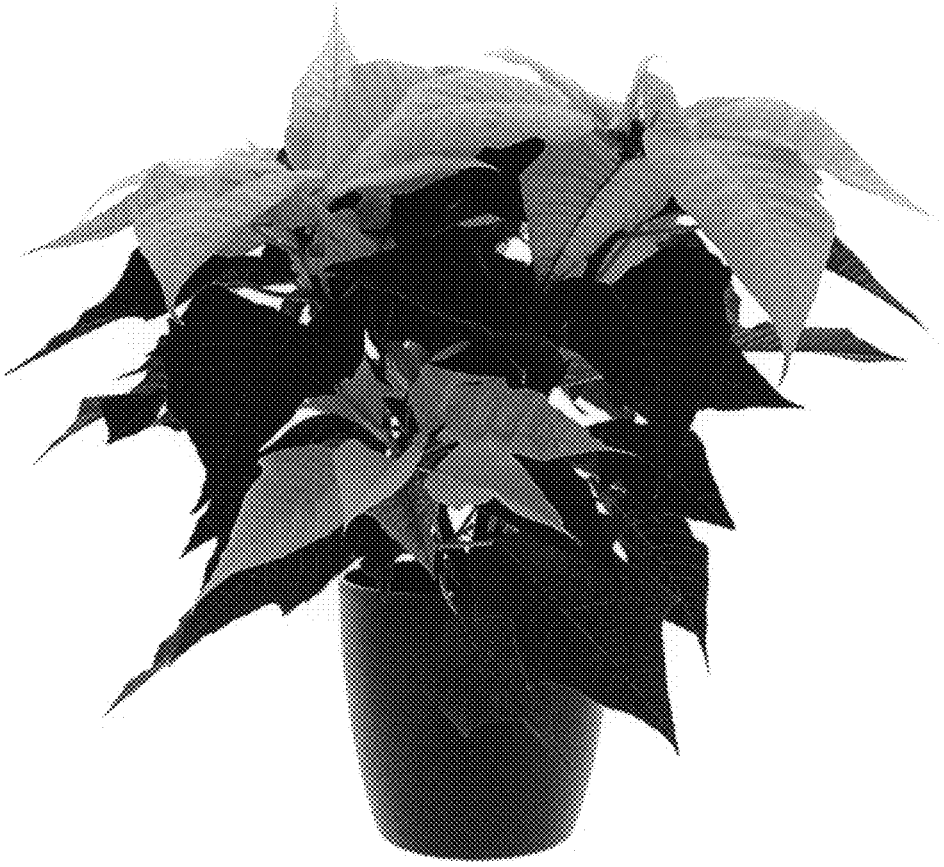

Botanical designation: *Euphorbia pulcherrima* Willd.
Cultivar denomination: 'BKPONVW'.

STATEMENT REGARDING PRIOR DISCLOSURES BY THE INVENTOR/APPLICANT & ASSIGNEE

An European Community Plant Breeder's Rights application for the instant plant was filed by the Assignee, Beekenkamp Plants B.V. of Maasdijk, The Netherlands on Nov. 19, 2020, application number 2020/2933. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of Poinsettia plant, botanically known as *Euphorbia pulcherrima* Wild. and hereinafter referred to by the name 'BKPONVW'.

The new Poinsettia plant is a product of a planned breeding program conducted by the Inventor in Maasdijk, The Netherlands. The objective of the breeding program is to create new uniform and freely-branching Poinsettia plants with good postproduction longevity.

The new Poinsettia plant originated from a cross-pollination made by the Inventor in February, 2013 in Maasdijk, The Netherlands of a proprietary selection of *Euphorbia pulcherrima* Willd. identified as code number 99-0263, not patented, as the female, or seed, parent with *Euphorbia*

*pulcherrima* Willd. 'Stargazer', disclosed in U.S. Plant Pat. No. 17,022, as the male, or pollen, parent. The new Poinsettia plant was discovered and selected by the Inventor as a single flowering plant within the progeny of the stated cross-pollination in a controlled greenhouse environment in Maasdijk, The Netherlands in January, 2014.

Asexual reproduction of the new Poinsettia plant by terminal vegetative cuttings in a controlled greenhouse environment in Maasdijk, The Netherlands since February, 2016 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'BKPONVW'. These characteristics in combination distinguish 'BKPONVW' as a new and distinct Poinsettia plant:

1. Broadly upright and uniformly mounding plant habit.
2. Moderately vigorous growth habit.
3. Freely branching habit.
4. Dark green-colored leaves.
5. Large and full inflorescences with white-colored flower bracts.
6. Excellent post-production longevity.

Plants of the new Poinsettia can be compared to plants of the female parent selection. Plants of the new Poinsettia differ primarily from plants of the female parent selection in the following characteristics:

1. Plants of the new Poinsettia are more upright than and are not as broad as plants of the female parent selection.

2. Plants of the new Poinsettia are more freely branching than plants of the female parent selection.
3. Plants of the new Poinsettia have white-colored flower bracts whereas plants of the female parent selection have orange red-colored flower bracts.

Plants of the new Poinsettia can be compared to plants of the male parent, 'Stargazer'. Plants of the new Poinsettia differ primarily from plants of 'Stargazer' in the following characteristics:

1. Plants of the new Poinsettia are more upright than and are not as broad as plants of 'Stargazer'.
2. Plants of the new Poinsettia are more freely branching than plants of 'Stargazer'.
3. Plants of the new Poinsettia have white-colored flower bracts whereas plants of 'Stargazer' have dark red-colored flower bracts.

Plants of the new Poinsettia can be compared to plants of *Euphorbia pulcherrima* Willd. 'BKPONSW', not patented. In side-by-side comparisons, plants of the new Poinsettia differ primarily from plants of 'BKPONSW' in the following characteristics:

1. Plants of the new Poinsettia are more freely branching than plants of 'BKPONSW'.
2. Flower bracts of plants of the new Poinsettia are more rugose than and not as smooth as flower bracts of plants of 'BKPONSW'.
3. Flower bracts of plants of the new Poinsettia are more white in color than flower bracts of 'BKPONSW'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet (FIG. 1) comprises a side perspective view of a typical flowering plant of 'BKPONVW' grown in a container.

Figure 2:
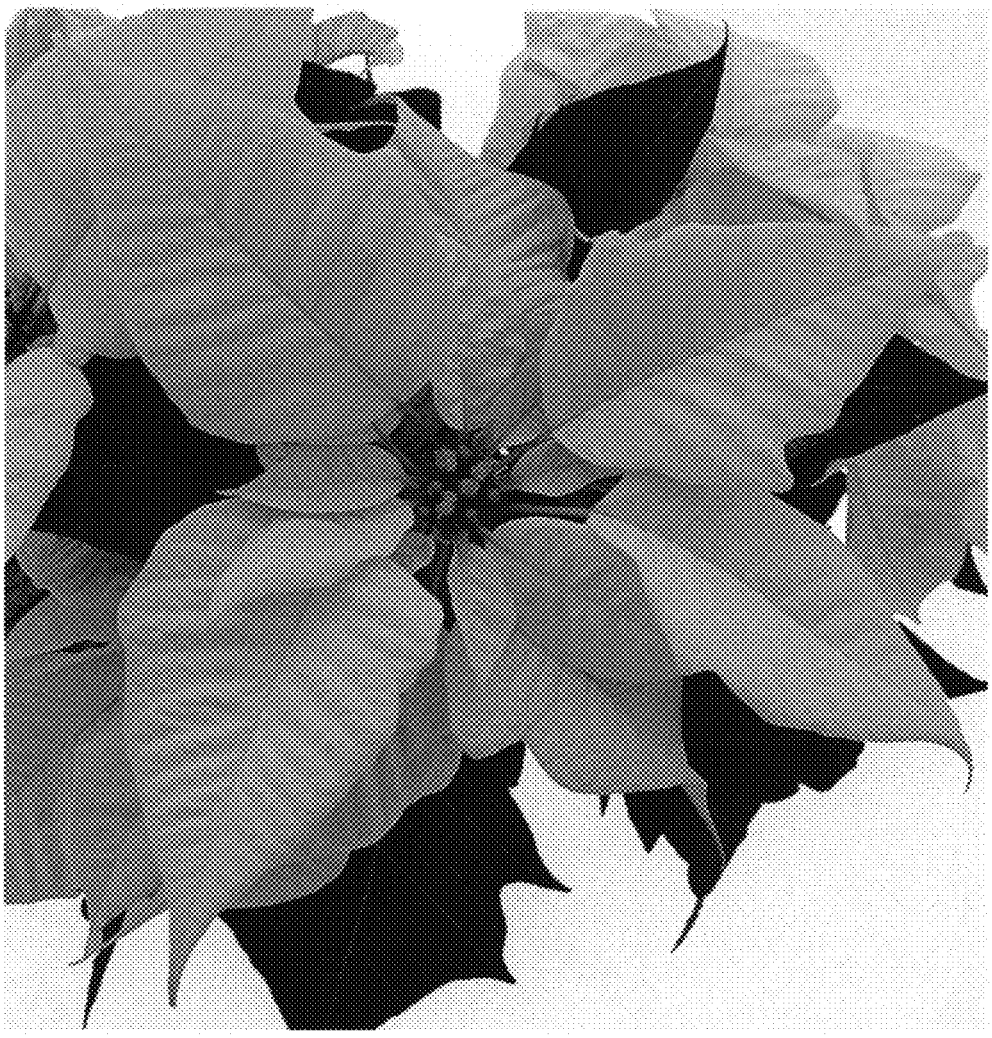

The photograph on the second sheet (FIG. 2) is a close-up view of a typical flowering plant of 'BKPONVW'.

DETAILED BOTANICAL DESCRIPTION

The aforementioned photographs and following observations and measurements describe plants grown during the late summer and autumn in 11-cm containers in a glass-covered greenhouse in Maasdijk, The Netherlands and under cultural practices typical of commercial Poinsettia production. During the production of the plants, day temperatures ranged from 17° C. to 18° C. and night temperatures ranged from 15° C. to 16° C. Plants were pinched one time and were 19 weeks old when the photographs and the detailed description were taken. In the following description, color references are made to The Royal Horticultural Society Colour Chart, 2015 Edition, except where general terms of ordinary dictionary significance are used.

Botanical classification: *Euphorbia pulcherrima* Willd. 'BKPONVW'.

Parentage:

*Female, or seed, parent.*—Proprietary selection of *Euphorbia pulcherrima* Willd. identified as code number 99-0263, not patented.

*Male, or pollen, parent.*—*Euphorbia pulcherrima* Willd. 'Stargazer', disclosed in U.S. Plant Pat. No. 17,022.

Propagation:

*Type.*—Terminal vegetative cuttings.

*Time to initiate roots, summer.*—About three weeks at temperatures about 19° C. to 21° C.

*Time to initiate roots, winter.*—About four weeks at temperatures about 19° C. to 21° C.

*Time to produce a rooted young plant, summer.*—About 20 days at temperatures about 17° C. to 19° C.

*Time to produce a rooted young plant, winter.*—About 30 days at temperatures about 17° C. to 19° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Broadly upright and uniformly mounded plant habit; inverted triangle with rounded crown; large full inflorescences positioned above the foliar plane; moderately vigorous growth habit and moderate growth rate.

*Plant height, soil level to top of foliar plane.*—About 25.8 cm.

*Plant height, soil level to top of floral plane.*—About 31 cm.

*Plant diameter or spread.*—About 41.6 cm.

*Lateral branch description.*—Branching habit: Freely branching habit, about five lateral branches develop after pinching. Length: About 21.2 cm. Diameter: About 6 mm. Internode length: About 1.5 cm. Strength: Moderately strong. Angle: Erect to about 60° from vertical. Texture and luster: Smooth, glabrous; glossy. Color, when developing: Close to 144B. Color, developed: Close to 146A.

*Leaf description.*—Arrangement: Alternate, simple. Length: About 12.7 cm. Width: About 9.8 cm. Shape: Ovate. Apex: Apiculate. Base: Obtuse to very short attenuate. Margin: Mostly entire; slightly to moderately undulate; occasionally with a single shallow to medium lobe on either side, sinuses divergent. Venation pattern: Pinnate. Texture and luster, upper surface: Smooth, glabrous; lamina, matte, and venation, slightly glossy. Texture and luster, lower surface: Slightly rugose, glabrous; lamina, matte and venation, slightly glossy. Color: Developing leaves, upper surface: Close to 137A. Developing leaves, lower surface: Close to 137B. Fully expanded leaves, upper surface: Darker than between 139A and N189A; venation, close to 138A. Fully expanded leaves, lower surface: Close to between NN137D and N138B; venation, close to 145A. Petioles: Length: About 5.8 cm. Diameter: About 3 mm. Strength: Moderately strong. Texture and luster, upper and lower surfaces: Smooth, glabrous; glossy. Color, upper surface: Close to 144A to 144B. Color, lower surface: Close to 144B.

Inflorescence description:

*Inflorescence type and habit.*—Large full inflorescences are compound corymbs of cyathia with white-colored flower bracts subtending the cyathia; one inflorescence per lateral branch with inflorescences positioned above and beyond the foliar plane and face mostly upright to slightly outwardly.

*Fragrance*.—None detected.

*Natural flowering season*.—Plants flower naturally during the late autumn into the winter under long nyctoperiod conditions; inflorescence initiation and development can be induced under artificial long nyctoperiod conditions; early flowering habit, response time is about 7.5 weeks.

*Post-production longevity*.—Excellent post-production longevity; plants of the new Poinsettia maintain good substance and bract color for about six weeks; flower bracts not persistent.

*Inflorescence width*.—About 26.9 cm.

*Inflorescence height*.—About 10.5 cm.

*Flower bracts*.—Quantity per inflorescence: About 14 to 19. Length: About 13.4 cm. Width: About 8.9 cm. Shape: Ovate. Apex: Apiculate. Base: Obtuse to truncate. Margin: Entire to slightly repand. Aspect: Mostly horizontal to slightly upright or slightly downward. Venation: Pinnate. Texture and luster, upper and lower surfaces: Slightly rugose, glabrous; matte. Color: Developing bracts, upper and lower surfaces: Close to between 1D and 154D. Fully expanded bracts, upper and lower surfaces: Close to between 1D and 150D; venation, close to between 1D and 150D; color becoming closer to between 2D and 150D with margins, close to 154D, with development. Bract petioles: Length: About 3.7 cm. Diameter: About 2 mm. Texture and luster, upper surface: Smooth, glabrous; glossy. Texture and luster, lower surface: Smooth, glabrous; moderately glossy. Color, upper and lower surfaces: Close to 144B.

*Cyathia*.—Quantity per corymb: About 10 to 15. Length: About 1.1 cm. Width: About 6 mm. Shape: Ovoid. Texture and luster, inner and outer surfaces: Smooth, glabrous; matte. Color, developing, inner and outer surfaces: Close to 143A; towards the apex, close to 144A; bracteoles, close to 54D. Color, fully developed, inner and outer surfaces: Close to 143A; bracteoles, close to 54D to slightly lighter than 54D. Nectaries: Quantity per cyathium: Typically one or two. Length: About 2 mm. Diameter: About 4 mm. Shape: Flattened. Texture and luster, inner and outer surfaces: Smooth, glabrous; matte. Color, developing, inner and outer surfaces: Close to 154B. Color, fully developed, inner and outer surfaces: Close to 9A to 9B.

*Pedicels*.—Length: About 3 mm. Diameter: About 2.5 mm. Strength: Moderately strong. Aspect: Erect to about 20° from vertical. Texture and luster: Smooth, glabrous; glossy. Color: Close to 144B.

*Reproductive organs*.—Stamens: Quantity per cyathium: About 20. Filament length: About 2 mm. Filament color: Close to 156D. Anther shape: Club-shaped. Anther size: About 0.5 mm by 1 mm. Anther color: Close to 153D. Amount of pollen: Moderate. Pollen color: Close to 13A. Pistils: To date, pistil development has not been observed on plants of the new Poinsettia. Seeds and fruits: To date, seed and fruit production has not been observed on plants of the new Poinsettia.

Pathogen & pest resistance: To date, plants of the new Poinsettia have not been shown to be resistant to pathogens and pests common to Poinsettia plants.

Temperature tolerance: Plants of the new Poinsettia have been observed to tolerate high temperature about 35° C. to 40° C. and to be suitable for USDA Hardiness Zones 10 to 12.

It is claimed:

1. A new and distinct Poinsettia plant named 'BKPONVW' as illustrated and described.

* * * * *